US010018584B2

(12) United States Patent
Bohets

(10) Patent No.: US 10,018,584 B2
(45) Date of Patent: Jul. 10, 2018

(54) OPTIMIZED UNIVERSAL ION-SELECTIVE ELECTRODE

(71) Applicant: Pion Inc., Billerica, MA (US)

(72) Inventor: Hugo Bohets, Antwerp (BE)

(73) Assignee: PION INC., Billerica, MA (US)

( * ) Notice: Subject to any disclaimer, the term of this patent is extended or adjusted under 35 U.S.C. 154(b) by 294 days.

(21) Appl. No.: 14/405,923

(22) PCT Filed: Jun. 14, 2013

(86) PCT No.: PCT/EP2013/062381
§ 371 (c)(1),
(2) Date: Dec. 5, 2014

(87) PCT Pub. No.: WO2013/186363
PCT Pub. Date: Dec. 19, 2013

(65) Prior Publication Data
US 2015/0185179 A1    Jul. 2, 2015

(30) Foreign Application Priority Data
Jun. 14, 2012 (GB) ..................................... 1210525

(51) Int. Cl.
G01N 27/333 (2006.01)
(52) U.S. Cl.
CPC .................................. G01N 27/333 (2013.01)
(58) Field of Classification Search
CPC .. G01N 29/00; G01N 27/333; G01N 27/3335; G01N 27/4163; B29C 35/00
See application file for complete search history.

(56) References Cited

U.S. PATENT DOCUMENTS

| 4,973,394 A | * | 11/1990 | Ross | G01N 27/3335 204/403.06 |
| 2008/0000290 A1 | * | 1/2008 | Nagels | G01N 27/333 73/61.61 |
| 2008/0149501 A1 | * | 6/2008 | Heule | G01N 27/4035 205/788.5 |
| 2009/0004751 A1 | * | 1/2009 | Leiner | G01N 21/783 436/133 |

FOREIGN PATENT DOCUMENTS

| EP | 1 965 198 A1 | 9/2008 |
| WO | 2005/103664 A2 | 11/2005 |
| WO | 2011/110517 A1 | 9/2011 |

OTHER PUBLICATIONS

Eugster, et al., Plasticizers for Liquid Polymeric Membranes of Ion-Selective Chemical Sensors, Analytica Chimica, vol. 289, No. 1, Apr. 20, 1994, pp. 1-13, Switzerland.
Eugster et al., "Plasticizers for liquid polymeric membranes of ion-selective chemical sensors", Analytica Chimica Acta, Switzerland, 289 (1994) 1-13.

* cited by examiner

Primary Examiner — Gurpreet Kaur
(74) Attorney, Agent, or Firm — Dinsmore & Shohl LLP

(57) ABSTRACT

The present invention relates to universal ion-selective electrode optimized for determinations of organic molecules. As opposed to the state of the art only one electrode composition is applicable to a variety of organic ions and ionizable molecules. It is accordingly an object of the present invention to provide an ISE composition that is optimized for the universal detection and determination of a very wide range of organic ions an ionizable organic molecules. As opposed to the state of the art this composition allows fast and sensitive detection of a very wide range of molecules independent of their chemical structure, class or number of charges. This optimized sensor can be used in different methodologies, e.g.: direct potentiometrie, standard addition, inline measurements and titration.

15 Claims, 7 Drawing Sheets

OPTIMIZED UNIVERSAL ION-SELECTIVE ELECTRODE

The present invention relates to universal ion-selective electrode optimised for determinations of organic molecules. As opposed to the state of the art only one electrode composition is applicable to a variety of organic ions and ionisable molecules. It is accordingly an object of the present invention to provide an ISE composition that is optimized for the universal detection and determination of a very wide range of organic ions and ionisable organic molecules. As opposed to the state of the art this composition allows fast and sensitive detection of a very wide range of molecules independent of their chemical structure, class or number of charges. This optimized sensor can be used in different methodologies, e.g.: direct potentiometrie, standard addition, inline measurements and titration.

BACKGROUND TO THE INVENTION

For the determination of ions in solutions, use is frequently made of the potentiometric ion-selective electrode (Cammann, K., Die Arbeit mit Ionenselektiven Elektroden [Working with ion-selective electrodes], 2nd ed., Springer Verlag: Berlin, Heidelberg, New York, 1977). Ion-selective electrodes are electrochemical sensors with which the concentration or activity of specific ions can be determined by means of a potential difference. The ion-selective potential difference occurs at the phase boundary between active electrode material/electrolyte and depends according to the Nernst equation on the activity of a specific ion in the solution. One example of sensors of this type are ion-selective field-effect transistors (for example DE 29344005 C2).

An ion-selective membrane is the key component of all potentiometric ion sensors. It establishes the preference with which the sensor responds to the analyte in the presence of various interfering ions from the sample. If ions can penetrate the boundary between two phases, then an electrochemical equilibrium will be reached, in which different potentials in the two phases are formed. Originally, ion-selective electrodes used glass or crystalline membranes, across which only the selected species of ion could migrate or be exchanged. Later, electrodes based on liquid ion-exchangers, also known as liquid-membrane electrodes, were introduced.

In the latter, the ion-exchange solution is immobilized within a polymer or ceramic membrane. The main component of said electroactive membrane is a neutral or charged compound, which is able to complex ions reversibly and to transfer them through an organic membrane by carrier translocation. This compound is called an ionophore or an ion carrier. There are two kinds of ionophores: charged one and neutral carriers. They are mobile in both free and complexed forms, so the mobilities of all species are part of the selectivity coefficient together with ion-exchange equilibrium. The mobile binding sites are dissolved in a suitable solvent and usually trapped in a matrix of organic polymer (gel). Ion activity measurements are performed predominantly in aqueous media, so all membrane constituents are lipophilic. Therefore, the primary interaction between the ion in water and the lipophilic membrane containing the ionophore is the extraction process.

Ionselective electrodes (ISEs) for the determination of organic ions or ionizable organic molecules are typically composed of an ion pair consisting of the analyte to be determined and a lipophilic counterion (e.g. tetraphenylborate). Consequently as a general rule during ISE development for each analyte the ISE matrix compositions needs optimization by introducing a certain amount of plasticizer specific for the analyte to be determined. Hence there is no general ISE composition, let it be a generally applicable plasticizer for a wide range of organic ions or ionizable organic molecules, i.e. a composition that is applicable across different organic ions and ionisable organic molecules.

Typical polymeric membranes are based on plasticized poly(vinylchloride) (PVC) and contain approximately 66% of an plasticizer and 33% of PVC. Such a membrane is quite similar to liquid phase, because diffusion coefficients for dissolved low molecular weight ionophores are in the order of $10^{-7}$-$10^{-8}$ cm$^2$/s. An appropriate plasticizer is added to a membrane in order to ensure the mobility of the free and complexed ionophore. It determines the membrane polarity and provides suitable mechanical properties of the membrane. The ionophore is usually present in 1% amount (approximately $10^{-2}$M), which is relatively low as compared to the glass electrode. An ion selective membrane can contain a salt of lipophylic anion and hydrophylic cation (additive), which improves performances of a membrane. Although other polymers like: polisiloxane, polystyrene, PMMA, polyamide or polyimide can be used as a membrane matrix, PVC is the most widely used matrix due to simplicity of membrane preparation.

As a results of the introduction of natural as well synthetic ionophores in ion-selective membranes, ISEs for direct measurement of various cations and anions were designed, and ISEs have found a wide field of applications, e.g. in clinical chemistry, electrophysiology, as detectors in ion chromatography, in highly selective transport processes through artificial membranes (also biological membranes), etc. . . . .

There are however, a number of disadvantages associated with the traditional liquid-membrane electrodes. For example, it is known that exudation of plasticizer and leaching of dissolved ionophores may ultimately limit the lifetime of carrier-based electrodes. The former process may lead to mechanical instability and electrode failure. In an effort to address this problem, the present inventors recently developed a liquid-membrane electrode having a gradient of the ionophores towards the sample contact surface and a decreasing gradient of electrically conducting particles towards the sample contact surface (PCT Publication WO 2005/103664). Such an electrode with a gradient polymer was shown to be extremely mechanically robust and sensitive, and particularly useful in HPLC, Capillary Electrophoresis and pharmaceutical applications such as dissolution testing.

However, said gradient polymer membrane electrode doesn't address a further disadvantage of the current liquid-membrane electrodes. As already explained hereinbefore, liquid-membrane electrodes are lipophilic in nature and therefore, the primary interaction between the ion in water and the lipophilic membrane containing the ionophore is the extraction process by the ionophore. Consequently, the selectivity of the ISE is predominantly determined by the ionophore. These ionophores are chosen to obtain high selectivity for only one ion, and are incorporated during electrode production. Such predefined matrixes are for example described in US 2002115224, wherein the sensor dots comprise a polymeric matrix and one or more (bio) chemical recognitions moieties (see [0021] of said US publication; and in EP1965198 directed to an optical-chemical carbon-dioxide sensor, and characterized in that the matrix comprises a pH-sensitive dye which can form an anionic species and a metal cationic species to interact with $CO_2$ in the sample to be analysed (see [0016] to [0019] of this European patent publication).

Another approach to obtain selectivity is the incorporation during sensor production of a lipophilic salt containing the analyte of interest, and to use a plastisizer optimized for that specific ion of interest. Using this approach only a few ions can be determined by pre defined electrodes where each ion requires a specific electrode. For practical and commercial reasons this methodology is inapplicable to the vast amount of organic ions an ionizable compounds. One way to come to an ISE universally applicable for a wide range of organic ions or ionizable organic molecules, is based on a post manufacturing conditioning of the ISE's as presented by Bohets et al. in PCT publication WO2011/110517.

However, when using this approach one departs from a predetermined matrix composition with no possibility to further optimize the membrane for a specific analyte. Consequently, using the base matrix composition as presented by Bohets et al. in WO2011/110517 only a limited applicability is encountered.

Electrodes constructed and conditioned according to Bohets et al. showed good results for lipophilic compounds such as Dapoxetine. However when used for less lipophilic compounds such as galantamine poor results were observed. In general, the performance of these electrodes is limited in high ionic background (0.1 M) and low pH, and for any practical purpose the usable range is limited to logP 2 (Logarithm of the octanol water partition) compounds.

It has accordingly been an object of the present invention to develop a base matrix electrode composition for use in the conditioning methodology of Bohets et al. (supra) that spans a very wide range of analytes to support a commercial viable universal ion selective electrode. It has thus been an objective of the present invention to realize a basic polymeric matrix, which can be conditioned and converted into an ion-selective polymeric matric sensitive to a wide range of analyst, using a post-manufacturing procedure.

BRIEF DESCRIPTION OF THE DRAWINGS

With specific reference now to the figures in detail, it is stressed that the particulars shown are by way of example and for purposes of illustrative discussion of the different embodiments of the present invention only, and are presented in the cause of providing what is believed to be the most useful and readily description of the principles and conceptual aspects of the invention. In this regard no attempt is made to show structural details of the invention in more detail than is necessary for a fundamental understanding of the invention, the description taken with the drawings making apparent to those skilled in the art how the several forms of the invention may be embodied in practice.

DESCRIPTION OF THE INVENTION

Figure 1:
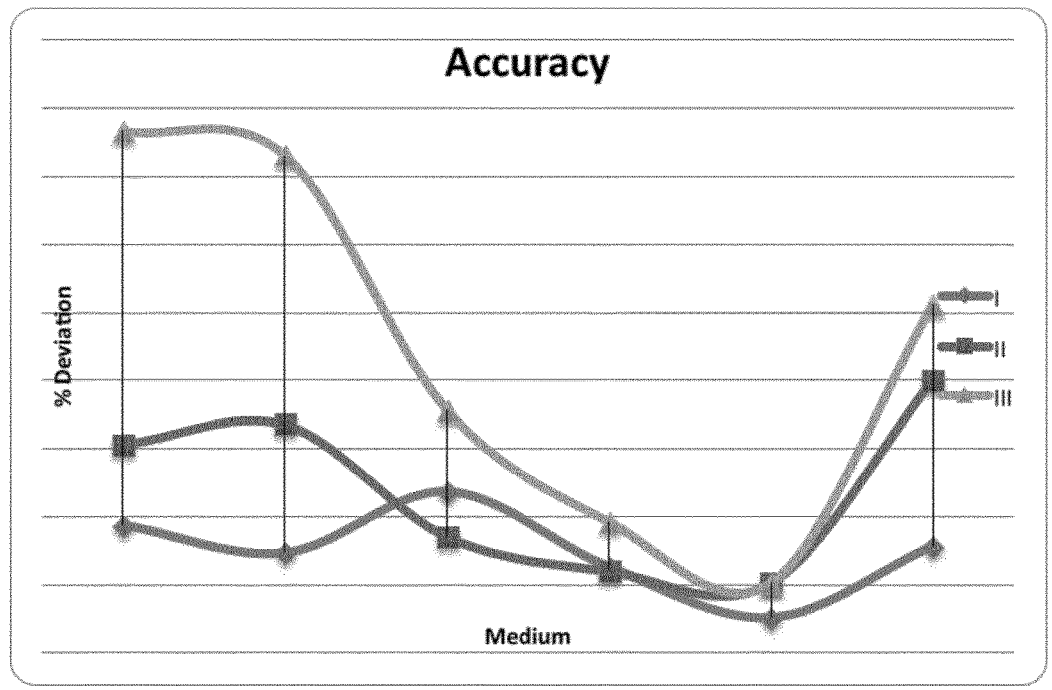
FIG. 1. Evaluation of slope, accuracy and sensitivity of ISE based on composition I, II and III when applied to the drug pseudoephedrine in different media.
Figure 1:
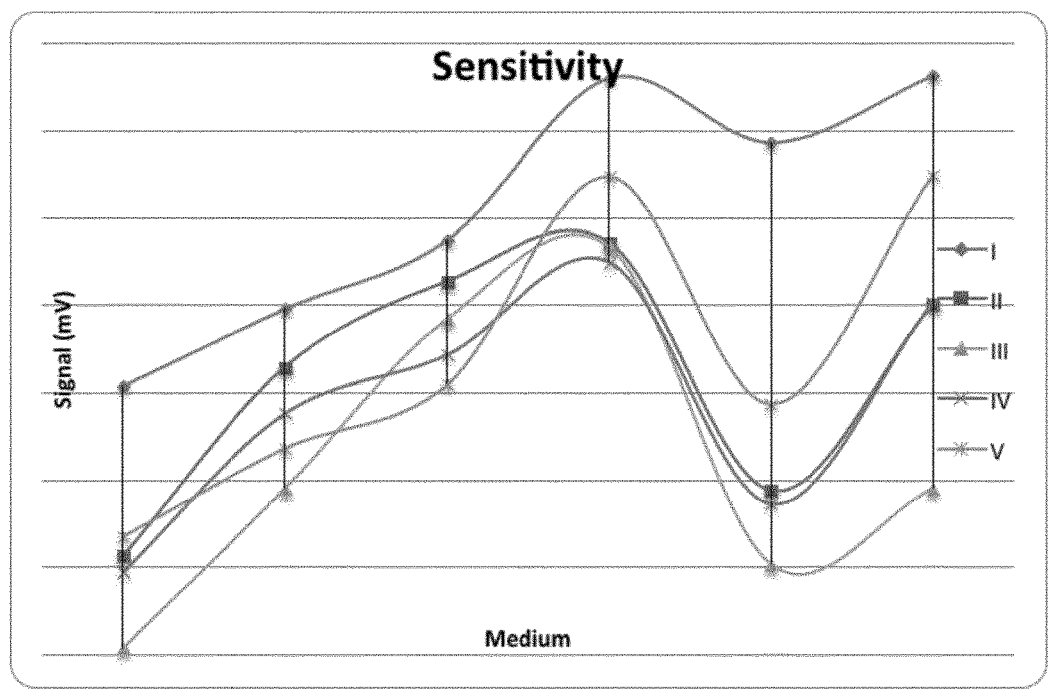
Figure 1:
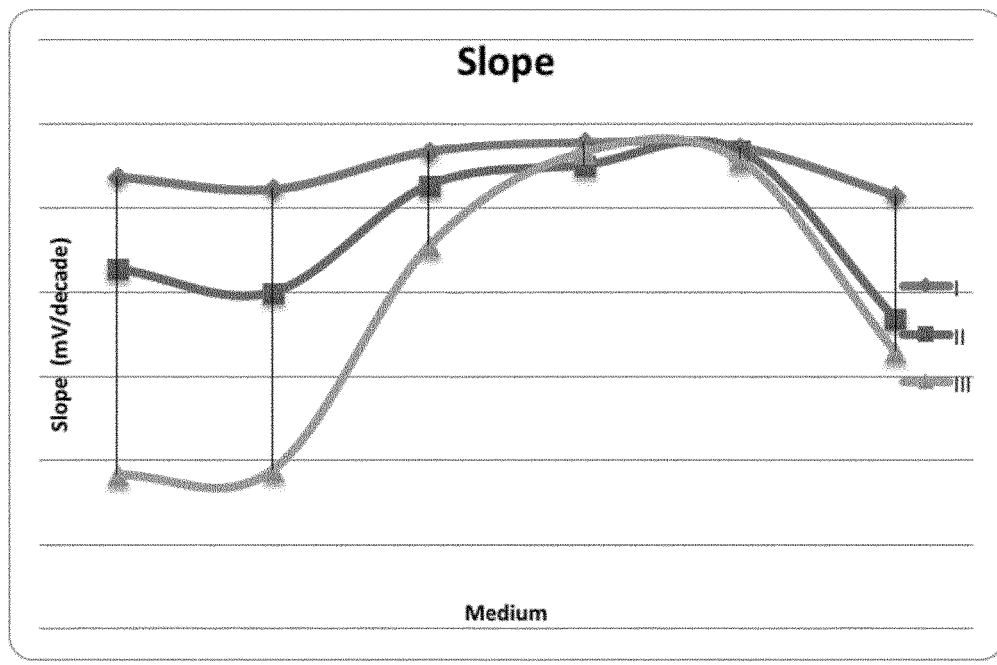

The present invention is based on the development of an ion-selective polymeric matrix wherein the ion-exchange solution is trapped in a matrix of organic polymer such as plasticized poly(vinylchloride) (PVC), and characterized in that it has an optimal composition for use as universal ion-selective electrode for the widest possible range of organic ions and organic ionisable molecules. As used herein, the wide range ion-selective polymeric matrix is meant to refer to a polymeric matric that can be made sensitive to a wide range of organic ions and ionisable organic molecules based on a post manufacturing conditioning of the ISE's. In other words, and different from the typical Ion Selective Electrodes, the matrix is not preloaded with the ionophore of interest, but through the presence of the given plasticizers the matrix compositions may be conditioned with said wide range of organic ions and ionisable organic molecules in a post manufacturing step. In addition, and in itself, the wide range ion-selective polymeric matrix can be used in titration, in particular when comprising ionically conducting particles as detailed hereinafter.

As shown in the examples hereinafter, incorporation of mesamoll and/or 2-(octyloxy)benzonitrile as main plasticizer in ion-selective polymeric matrices will generate an electrode, which is more accurate, sensitive and robust than those containing a commonly used plasticizer, when determining organic ions and organic ionisable molecules. Thus based on the use of mesamoll and/or 2-(octyloxy)benzonitrile as main plasticizer in ion-selective polymeric matrices, a wide range ion-selective polymeric matrix with unique properties has been obtained.

Thus in a first aspect the present invention provides the use of mesamoll and/or 2-(octyloxy)benzonitrile in, and the realization of a wide range ion-selective polymeric matrix, i.e. an ion-selective polymeric matrix sensitive to organic ions and ionisable organic molecules with logP values above 0; and characterized in that the polymeric material comprises mesamoll and/or 2-(octyloxy)benzonitrile; in particular mesamoll.

As used herein organic ions and ionisable organic molecules are molecules which logP ranges upwards from 0; in particular organic ions with logP ranges from 0-7. It ranges from but is not limited to any molecule containing one or more functional groups selected from: primary, secondary and tertiary amines, quaternary ammonia, and organic borates of the type $B(R)_4^-$. Compounds with these functional groups may belong to following types: aromatic compounds, aliphatic compounds, as well as compounds that combine aliphatic and aromatic features, it accordingly ranges from pharmaca over food additives to surfactants. There field of application could be very wide such as medicinal compounds, tensides, and reagents.

In an alternative embodiment the wide range ion-selective polymeric matrix as described herein may further comprise electrically conducting particles. In principle any art known electrically conducting particles typically used in the manufacture of ion-selective electrodes can be used, such as for example made of gold, silver, glassy carbon, graphite, copper, carbon nanotubes and nanowires. Said electrically conducting particles can be present in an amount up to 80% wt; a particular embodiment being up to 10% wt of carbon nanotubes or carbon nanowires In another embodiment the wide range ion-selective polymeric matrix as described herein may further comprise ionically conducting particles such as conductivity increasing salts; in particular conductivity increasing salts that are lipophilic of nature such as ETH 500 (tetradodecylammonium tetrakis(4-chlorophenyl)borate), borates ($BR_4^-$), quaternary ammonia and the like. Said ionic conducting particles (salts) can be present in an amount up to 30% wt; in particular up to 20% wt.

In principle any art known polymer matrix used in the manufacture of liquid-membrane electrodes can be used, and include for example the application of one or more of poly(n-butylacrylate), cross-linked poly(butylacrylate), polycarbonate, polystyrene, polymethylmethacrylate, poly(vinylchloride-co-vinylacetate-covinylalcohol), polysiloxane, polyvinyl chloride, or high molecular weight polyvinyl chloride; in particular polyvinyl chloride, or high molecular weight polyvinyl chloride.

Accordingly in a further embodiment the wide range ion-selective polymeric matrix of the present invention is further characterized in that the polymeric component of said polymeric matrix is made from a polymer selected from the group consisting of poly(n-butylacrylate), cross-linked poly(butylacrylate), polycarbonate, polystyrene, polymethylmethacrylate, poly(vinylchloride-co-vinylacetate-covinylalcohol), polysiloxane, polyvinyl chloride, high molecular weight polyvinyl chloride, or combinations thereof; in particular polyvinyl chloride, or high molecular weight polyvinyl chloride.

As will become evident form the examples hereinafter, the polymeric component is present within the typical range seen in ion-selective electrodes and the polymeric matrix comprises of about 20 to about 40% of polymer. The plasticizers mesamoll and/or 2-(octyloxy)benzonitrile being important to create the desired environment are present within a range of about 50 to about 70% of the polymeric matrix, in particular of about 60 to about 65%.

For the avoidance of doubt, and as evident from the examples hereinafter, the matrix may comprise further components typically found in ISE's such as common plasticizers, conductivity increasing salts, ionically conducting particles, and ionophoric molecules. Such further common plasticizers include, but are not limited to dioctyl sebacate (DOS), bis(2-ethylhexyl)phthalate (DOP), tris(2-ethylhexyl) phosphate (TOP) or tris(2-ethylhexyl)trimellitate (TOTM) but when present, these further plasticizers would only amount up to about 20%, in particular only up to about 15%, more in particular only up to about 10%, even more in particular only up to about 5% of the mesamoll and/or 2-(octyloxy)benzonitrile plasticizer present in the matrix.

In the liquid-membrane electrode according to the present invention, the polymeric matrix preferably comprises of about 20 to about 40% of polymer and of about 0.01 to 5.0% of ionophore. Addition of conductivity increasing salts such as ETH 500 can be present in an amount up to 20%. The polymeric component in the matrixes as described herein preferably consists of polyvinyl chloride, or high molecular weight polyvinyl chloride. The ionophore as used in the matrixes of the present invention preferably consists of Potassium tetrakis[3,5-bis(trifluoromethyl)phenyl]borate. The ionically conducting particles as used in the matrixes of the present invention preferably consists of ETH 500.

The ion-selective polymeric matrixes according to the present invention can be applied in any type of electrodes, including classical internal solution sensors, Coated wire sensors and gradient based sensors such as described in WO 2005/103664. In other words, there is no particular limitation as to the building of an ion-selective electrode comprising the polymeric matrix as described herein. In a particular embodiment the ion-selective electrode is a gradient matrix electrode made in accordance with the methodology described in WO 2005/103664; and accordingly characterized in that the ion-selective polymeric matrix comprises a gradient of electrically conducting particles, which increase in concentration away from a sample contact surface.

For the coated wire sensor typical components such as but not limited to gold, silver, glassy carbon, graphite can be used as conductive substrate. Possible insulator to be used in such coated wire sensors include, but are not limited to Polytetrafluoroethylene (PTFE), Polypropylene, poly(n-butylacrylate), cross-linked poly(butylacrylate), polycarbonate, polystyrene, polymethylmethacrylate, poly(vinylchloride-co-vinylacetate-covinylalcohol), polysiloxane, polyvinyl chloride, or high molecular weight polyvinyl chloride; in particular polyvinyl chloride, or high molecular weight polyvinyl chloride can be used.

Dependent on the application, such as for example upon application in a classical internal solution sensors, the polymeric matrix may already comprise ionophoric molecules (e.g.: Potassium tetrakis[3,5-bis(trifluoromethyl)phenyl]borate) for the organic ions and ionisable organic molecules of interest. In said embodiment the ionophores are present in an amount of about 0.01 to 5.0% by weight of the polymeric matrix. In a particular embodiment the matrix is used in a gradient matrix electrode made in accordance with the methodology described in WO 2005/103664; and accordingly characterized in that it comprises a gradient of ionophore molecules, which increase in concentration towards a sample contact surface.

Thus in a specific embodiment, the present invention provides a wide range ion-selective polymeric matrix, having;
a gradient of electrically conducting particles, which increase in concentration away from a sample contact surface;
a gradient of ionophore and plasticizer molecules, which increase in concentration towards a sample contact surface; and characterized in that;
that the polymeric material comprises the plasticizers mesamoll and/or 2-(octyloxy)benzonitrile; in particular mesamoll.

In this gradient matrix the ionophores are present in an amount of about 0.01 to 5.0% by weight; the electrically conducting particles are present in an amount of about 20 to 80% by weight; and the plasticizers mesamoll and/or 2-(octyloxy)benzonitrile are present within a range of about 50 to about 70% of the polymeric matrix.

In a particular embodiment of this gradient matrix, the plasticizers mesamoll and/or 2-(octyloxy)benzonitrile are present in an amount of about 60 to about 65% by weight and consists of mesamoll. In a more particular embodiment this gradient matrix is further characterized in that the polymer component in the polymer matrix is present in an amount of about 20 to about 40% by weight and consists of polyvinyl chloride, or high molecular weight polyvinyl chloride. In a particular embodiment the electrically conducting particles being present in gradients ranging from 80-0%, 80-10%, 80-20%, 60-20%, 60-10% (preferred), 60-0% (most preferred), 40-0%, 40-5% 40-10%, 10-0%, 10-1%, 10-2% of conducting particles throughout the matrix, the lowest concentration at the sample contact surface.

Evidently, in a further aspect the present invention provides the use of the wide range ion-selective polymeric matrix as described herein in the manufacture of a potentiometric electrode. Given the sensitivity of the matrix to organic ions and ionisable organic molecules with logP values above 0 in general, it can be used in different methodologies, such as for example direct potentiometric, standard addition, inline measurements and titration.

Thus in a further aspect the present invention provides the use of the wide range ion-selective polymeric matrix as described herein in a potentiometric method selected from the group consisting of direct potentiometric, standard addition, inline measurements, titration and the like.

When used in titration, the wide range ion-selective polymeric matrix comprises;
   ionophores present in an amount of about 0.01 to 5.0%; in particular of about 0.05 to 0.5%;
   Ionically conducting particles, in particular conductivity increasing salts such as ETH 500, in an amount of about 1.0 to about 20.0%; more in particular in an amount of about 1.0 to about 10.0%; even more in particular in an amount of about 5.0%;
   a polymer, in particular polyvinyl chloride, or high molecular weight polyvinyl chloride, in an amount of about 20 to about 40%; in particular of about 25 to 35%; and characterized in that;
   the polymeric material comprises the plasticizers mesamoll and/or 2-(octyloxy)benzonitrile; in particular mesamoll.

Within this titration embodiment, the plasticizers mesamoll and/or 2-(octyloxy)benzonitrile are typically present in an amount of about 60 to about 65%; more in particular in an amount of about 61%. The percentages as used herein are % weight of solid.

The present invention is further characterized by reference to following examples. It should be noted however that the invention as described and claimed herein is not limited in scope by the specific embodiments. The presentation of examples is thus solely intended as illustration of possible applications of the invention and any similar or equivalent embodiments are considered to fall within the scope of the present invention. Modifications of the invention beyond those shown and defined in examples will be obvious to those skilled in the art based on previous description of the invention. Such modifications are equally considered to be comprised within the scope of the invention.

Exemplary Embodiments of the Invention

Matrix Development

As already mentioned hereinbefore, it has been an object of the present invention to try and develop a matrix component that allows a universal application in the determination of organic molecules and in particular low logP organic molecules. Using the currently available matrixes potentiometric determination of such compounds is problematic and requires optimization of the matrix for each ion of interest.

In order to select the optimal ion selective cocktail for a wide range of organic ions or ionisable organic molecules with a low logP, the plasticizers: 2-nitrophenyl octyl ether, dibutyl butanephosphonate, dipentyl phthalate, octyl-(2-(trifluormethyl)phenyl)ether, 2-(dodecyloxy)benzonitrile, bis (1-butylpentyl)adipate, dioctyl phthalate, dioctyl phenylphosphonate, tris(2-ethylhexyl)phosphate, Mesamoll (mesamoll being a phthalate-free general purpose plasticizer, mainly consisting of an alkylsulphonic acid ester with phenols, in particular ASE having the CAS-Reg.-No.: 091082-17-6), Tris(2-ethylhexyl)trimellitate, tritolyl phosphate, 2-(octyloxy)benzonitrile and Bis(2-ethylhexyl) sebacate, 2- where evaluated.

Representative examples of organic ions or ionisable organic molecules with a low logP used for this study include procaterol, etilefrine, pseudoephedrine, ranitidine atropine, ritrodrine, ephedrine, galantamine. Two higher logP compounds were also added to the study: paliperidone and dapoxetine.

Were we expected to find a structure activity relation between the structure of the plasticizer and the response of the ISE, no such correlation was actually found. Instead and to our surprise, a few plasticizers yielded significantly better results for all the analytes when compared to the bulk of the plasticizers. From this study two clear universally applicable plasticizers emerged; 2-(octyloxy)benzonitrile and mesamoll. This universal applicability is contrary to the behavior of the bulk of the plasticizers and opposed to the common conception that each organic ion needs a dedicated (selected) plasticizer.

The thus identified universal plasticizers and tritolyl phosphate where selected for further investigation. These where compared with a state of the art electrode such as for example described in H. Bohets, K. Vanhoutte, R. De Maesschalck, P. Cockaerts, B. Vissers, L. J. Nagels Development of in situ selective sensors for dissolution Anal. Chim. Acta, 581 (2007), pp. 181-191.

The following 4 compositions were used:
I 32% wt PVC, 2% wt Potassium tetrakis(4-chlorophenyl) borate, 65% wt Mesamoll (Alkylsulfonic phenyl ester)
II 32% wt PVC, 2% wt Potassium tetrakis(4-chlorophenyl) borate, 65% wt Tris(2-ethylhexyl)trimellitate
III Electrode composition of Bohets et al.
IV 32% wt PVC, 2% wt Potassium tetrakis(4-chlorophenyl) borate, 65% wt tritolyl phosphate
V 32% wt PVC, 2% wt Potassium tetrakis(4-chlorophenyl) borate, 65% wt 2-(octyloxy)benzonitrile These compositions where applied in gradient based electrodes and constructed as described in patent application WO2011/110517. Conditioning was done at room temperature over at least 1 days.

Extensive comparison of different sensors was done for three drugs that are difficult to measure by the state of the art electrode; Ranitidine, Psudoephedrine, Galantamine. This for a wide variety of media such as: 1, 10, 100 mM HCl, 10 mM acetate buffer pH5, 10 mM phosphate pH7.

For these media the electrodes where evaluated on accuracy, sensitivity, adequate speed and slope (as measure for selectivity).

Figure 2:
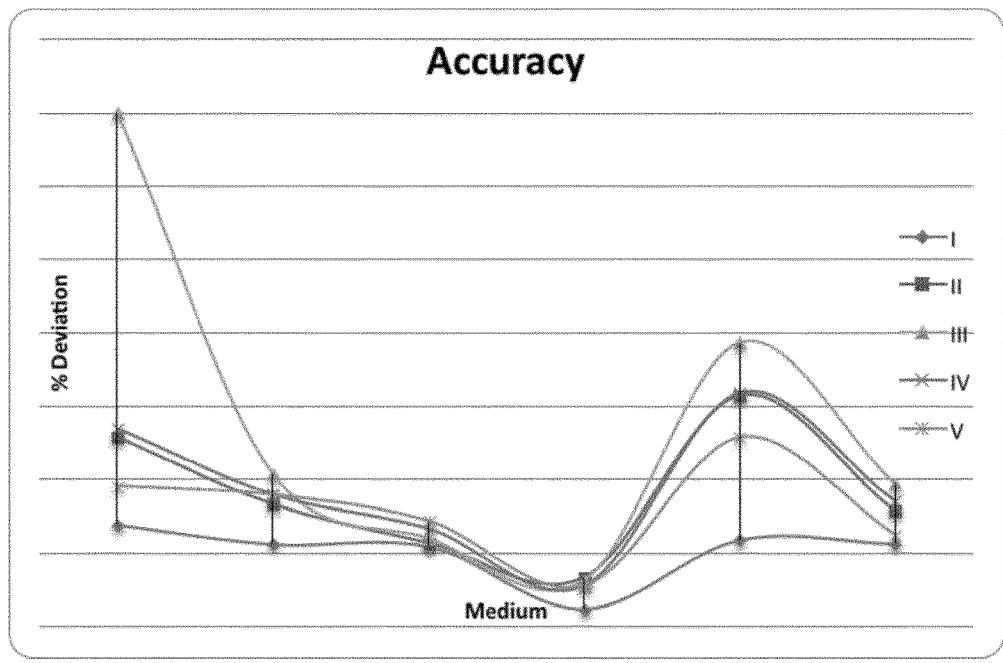
FIG. 2. Evaluation of slope, accuracy and sensitivity of ISE based on compositions I, II, III, IV and V when applied to the drug ranitidine in different media.
Figure 2:
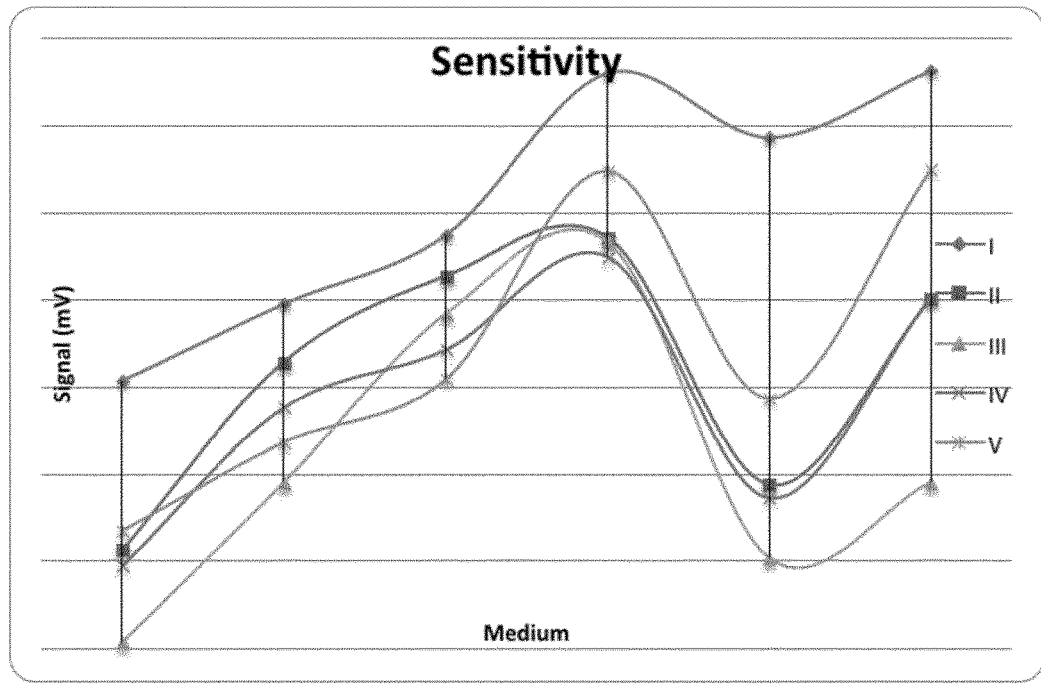
Figure 2:
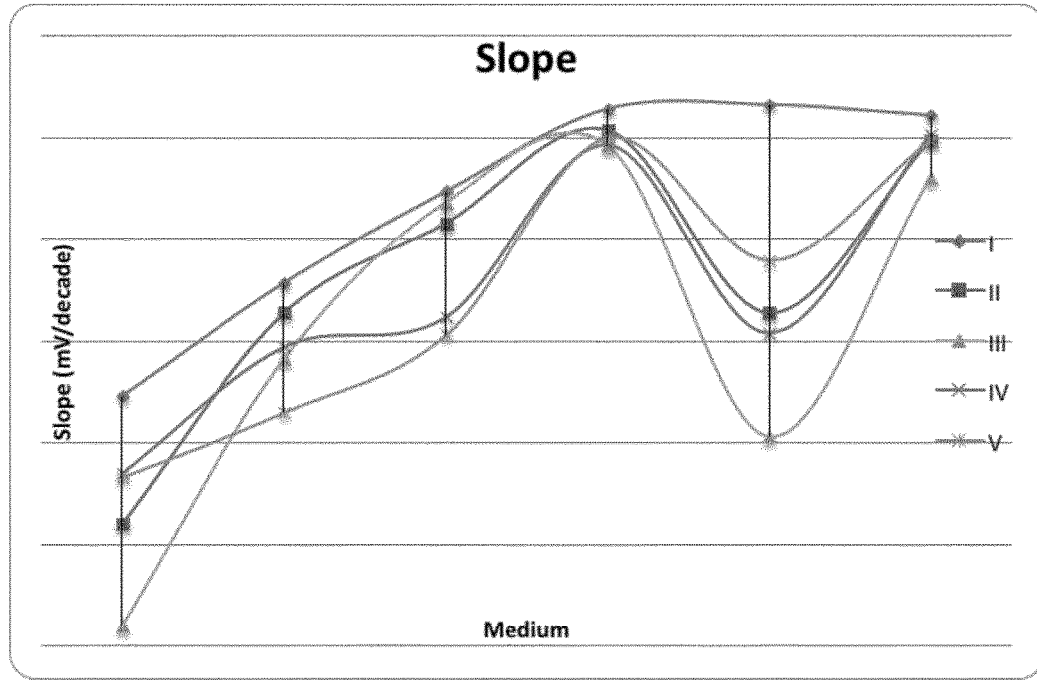

Typical finding for Pseudo Ephedrine are summarized in FIGS. 1A-C, and show that for all aspects composition I is superior to the others Typical finding for Ranitidine are summarized in FIGS. 2A-C, and show that for all aspects composition I is superior to the others For all aspects composition I is superior to the others After these tests composition I was assigned as optimal composition for the universal ion selective electrode.

Further testing of this composition on the drugs on: dapoxetine, loperamide, diphenhydramine, cinnarizine, meclizine, cyclizine and verampil showed excellent results (data not shown). Therefore we can conclude that this sensor has a optimized composition for a wide application range.

Surprisingly the best plasticizer for low logP drugs (<2) also performs superior for the high logP compounds, hence we can assign 2-(octyloxy)benzonitrile and Mesamoll as universal ion selective plasticisers for organic ions and organic ionisable compounds.

Surprisingly influence of anorganic ions on the response of the ISE formulations is least pronounced for the ISE containing mesamoll. More surprising was the improved behaviour of the mesamoll sensor in tenside containing media as compared with standard plasticisers.

Sensor Optimization

Figure 3:
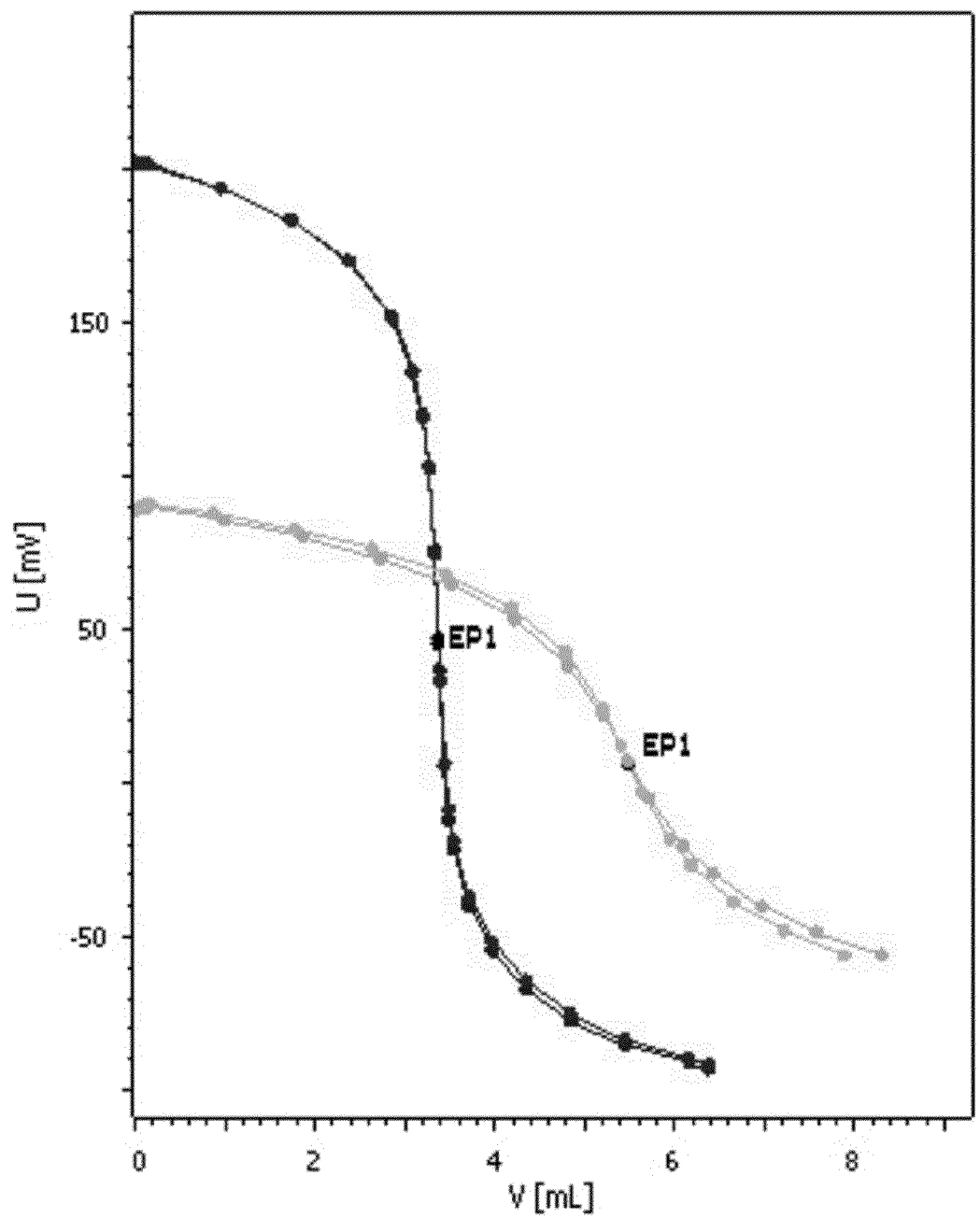
FIG. 3: Titration of 1 mg diphenhydramine by means of the Octens ISE (Black) and 2 mg diphenhydramine by means of the NIO electrode (Grey).

A further Optimisation of sensor composition I is: 5% wt ETH 500 31 wt % PVC 61% wt mesamoll an 0.1% wt Potassium tetrakis[3,5-bis(trifluoromethyl)phenyl]borate. As shown in FIG. 3, this formulation (composition VI) is excellent for use in titrations and is vastly superior to the present state of the art the NIO of Metrhom.

This effect is especially pronounced when our electrode is used in combination with Potassium tetrakis(4-chlorophenyl)borate as titrant.

Due to the high resistivity of mesamoll towards saponification, the sensor can be used in pH ranges up to 14.

Table 1 further illustrates the true universal capability of the sensor based on the wide range ion-selective polymeric matrix of the present invention, when for example used as an endpoint indicator for titration. The components titrated with an electrode based on sensor composition VI, range over a wide variety of organic ions with divers physic chemical parameters (logP 0-5, anions/cations, mono/divalent, . . . ), ranging from pharmaca over food additives to surfactants.

Even non-charged organic species are titrated by use of this sensor (Tween 20®) as well as complexes of cations ($ZnO_{2+}$, $Zn^{2+}$). In the present state of the art there is one ISE dedicated to each application: Tween 20®, pharmaca, surfactants, . . . . The fact that we can do all those divers titrations using one ISE proofs the truly universal character of the invention for the titration application.

TABLE 1

Examples of components titrated with the electrode of composition VI.

| Component | Tested range (ppm) | Relative standard deviation (%) |
| --- | --- | --- |
| Pharmaceuticals | | |
| Cinnarizine | 10-50 | 0.16 |
| Dapoxetine | 1.5-38 | 0.14 |
| Diphenhydramine | 7-50 | 0.20 |
| Loperamide | 1-5 | 0.7 |
| Ranitidine | 10-150 | 0.44 |
| Food additives | | |
| Quinine in Tonic | 2.2-110 | 0.18 |
| Philabuster ® on fruit | 10-150 | 0.14 |
| Philabuster ® in apple juice | 1-4 | 2.5 |
| Acesulfame K | 30-250 | 0.18 |
| Saccharine | 60-300 | 0.5 |
| Surfactants | | |
| Tween 20 ® | 100-1000 | 0.07 |
| Sodium lauryl sulfate | 2-20 | 0.35 |
| Metal ions | | |
| $Zn^{2+}$ | 3-30 | 1.7 |
| $Cu^{2+}$ | 6-30 | 2.55 |
| $Ba^{2+}$ | 3-30 | 0.5 |
| $ZrO^{2+}$ | 6-60 | 2.12 |

Furthermore we can use one and the same ISE for all the applications and convert it with ease from one application to the next. A wide range of titrants was used to obtain these results: sodium tetraphenyl borate, TEGO®, quaternary ammonia, potassium tetrakis 4-chlorophenyl borate, and combinations of one of the above with any complexant such as crown ethers, calixarenes, carboxylic acids, . . . . When combined with the right lipophilic reagents, even hydrophilic compounds with negative logP such as metal ions and acesulfame K can be determined by the electrode of the invention.

Comparison to State of the Art ISE's

Figure 4:
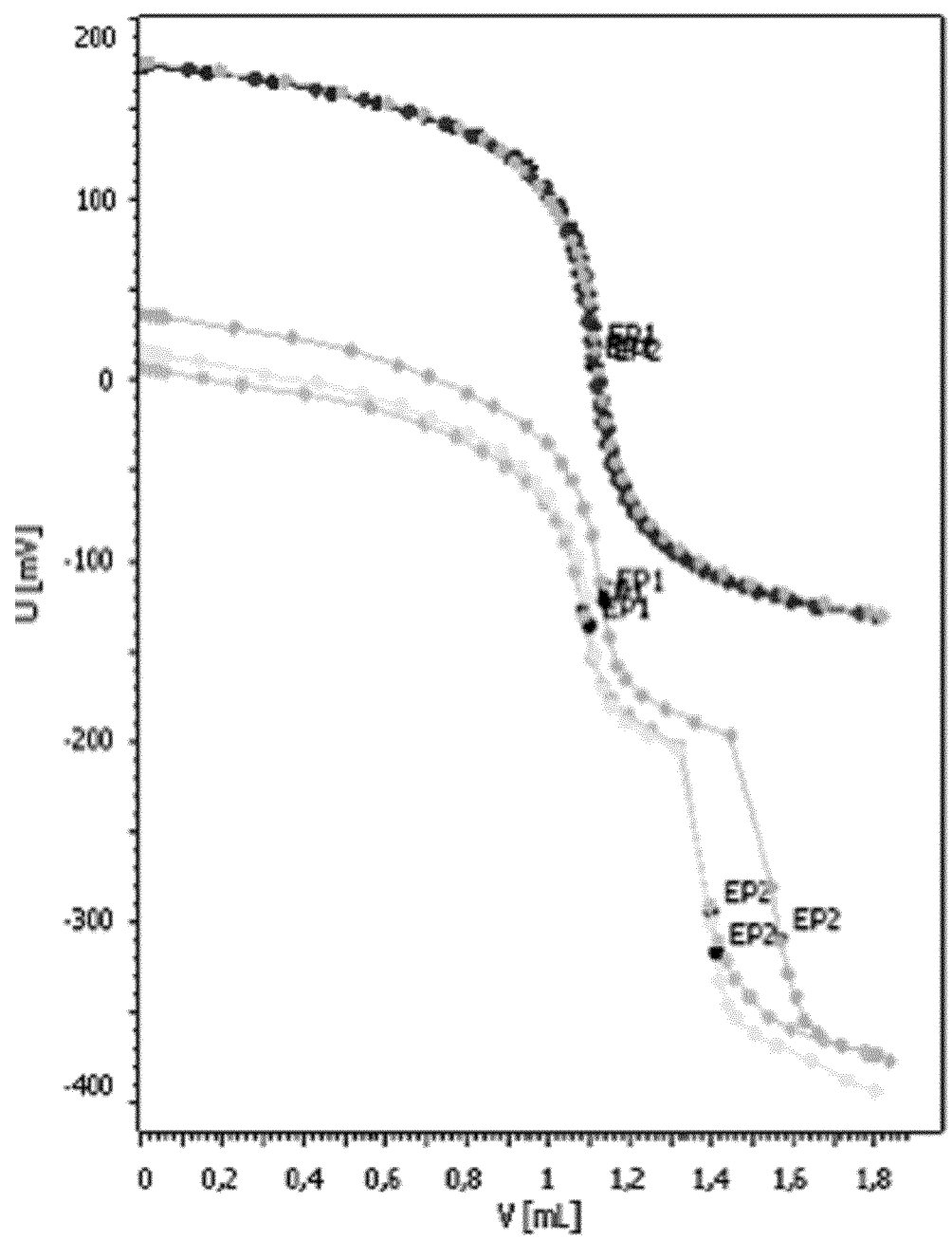
FIG. 4: Potentiometric titration curves of 320 µg papaverine in 20 mL 0.01 M HCl; Top: using the electrode according to this invention, Bottom: using the Ionic Surfactant electrode from Metrohm.

State of the art ISE's, such as the Ionic Surfactant Ion Selective Electrode of Metrohm USA Inc., include ionophores in the matrix that makes them selective towards one reagent or a class of analytes. Hence those sensors are not universal as the sensor of present invention is. A major drawback of the state of the art specific ionophore sensors is that they don't cope well with change of reagent. Upon use of a different than the prescribed reagent they have irreproducible EP's, require an unpractical high amount of conditioning titrations and exhibit phantom EP's. This is clearly illustrated in FIG. 4, wherein said Metrohm Ionic Surfactant electrode is compared with the universal electrode according to this invention in the titration of 320 μg papaverine in 20 mL 0.01 M HCl.

Figure 5:
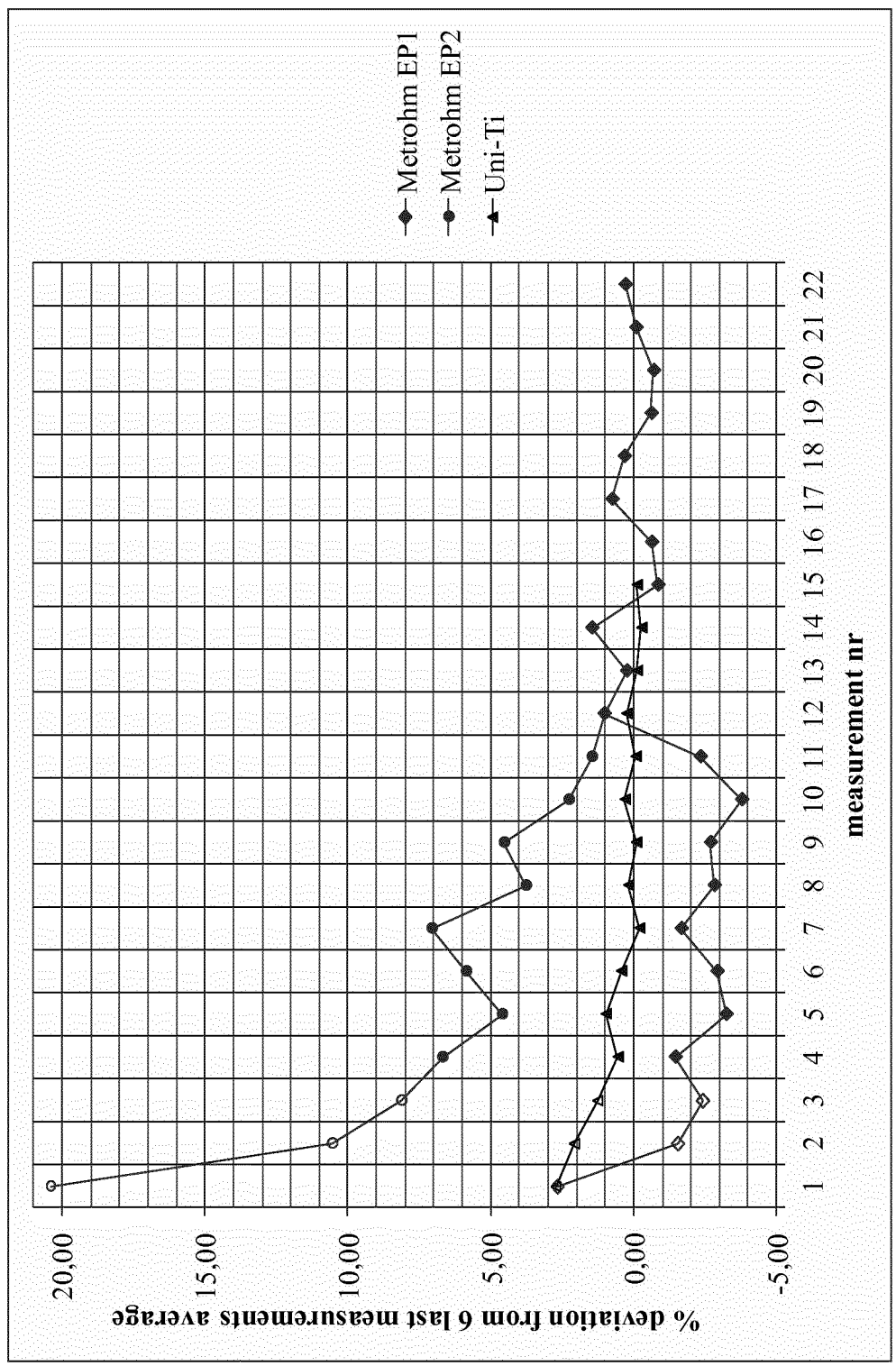
FIG. 5: Resulting deviation in percent (%) for the Uni-Ti (triangles) and Ionic Surfactant electrode (dots) including the first three titrations. Deviation is calculated from the average of the last 6 measurements (each ISE calculated separately).

To exclude that these deviations would disappear after limited time, a full evaluation of the titrations of 320 μg papaverine in 20 mL 0.01 M HCl was made on 15 day period. The results were compared to the data obtained for an electrode made according to this invention. From FIG. 5 it is clear that after 15 days of use, the Metrohm Ionic Surfactant electrode is still not adapted to the new reagent, resulting in double and/or poor producible EP's. This irreproducible behavior makes the present electrodes unpractical to useless in a commercial setting where a multitude of reagents are needed.

Sensitivity of the Matrix

Figure 6:
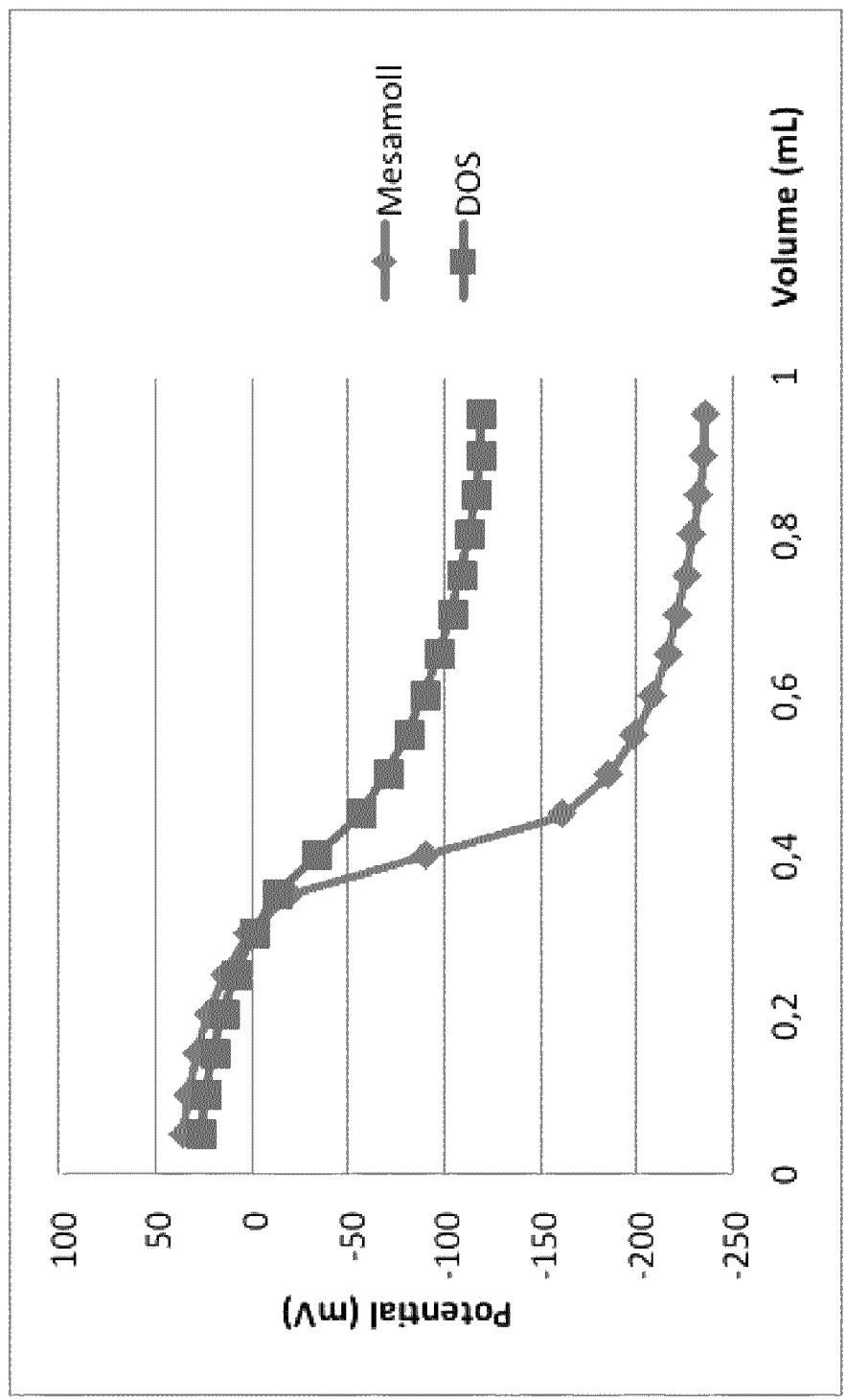
FIG. 6: Titration of 250 µg diphenhydramine; comparison between a DOS and Mesamoll based sensor.

The sensors of the invention are not only precise and accurate, they are also more sensitive then ISE containing common plasticizers used in ISE. This is illustrated in FIG. 6 where the titration response of a sensor of the present invention based on composition VI is compared to a sensor containing dioctyl sebacate (DOS) as plasticizer.

Effect of Electrically Conducting Particles in the Matrix

In a further example electrically conducting particles, i.e. carbon nanotubes, were incorporated in the matrix composition, thus providing a composition comprising 40% wt PVC, 50% wt mesamoll and 10% wt of the further electrode components being the sum of salts, ionophores and carbon nanoparticles. A 10% solution in an organic solvent of this polymeric composition was deposited in multiple steps of a total volume of about 10 μl on a cylindrical PVC electrode body with a diameter of 3 mm comprising a central 1 mm wide graphite-PVC composite cylinder.

Surprisingly the incorporation of carbon nanotubes doesn't affect the performance of the ISE in titration applications but does reduce the impedance of the sensor. Also addition up to 20% wt ETH 500 doesn't reduce significantly the performance of the ISE. It was further found that this electrode could resist two-phase mixtures of organic solvent/water. Use of hexane has no or little influence on the sensor. Methyl isobutyl ketone, chloroform and toluene damage the sensor slowly, hence titrations in these types of two phase systems can be done for a limited time (approximately 100 titrations).

The invention claimed is:

1. A method of making an ion-selective electrode for detecting organic ions and ionisable organic molecules comprising:
providing a Mesamoll plasticizer in an ion-selective polymeric matrix comprising 32% by weight of a Poly(vinylchloride) polymer, 65% by weight of said plasticizer, 2% by weight of an ionophoric potassium tetrakis (4-chlorophenyl)borate molecule and comprising one or more conductivity increasing salts, wherein said ion-selective polymeric matrix is sensitive to organic ions and ionisable organic molecules with logP values above 0, wherein said ion-selective polymeric matrix is not preloaded with said organic ions or said ionisable organic molecules with logP values above 0; and
incorporating said ion-selective polymeric matrix in the ion selective electrode.

2. The method according to claim 1, wherein said conductivity increasing salts are present in an amount up to 20% by weight.

3. The method according to claim 1, wherein the polymeric matrix further comprises electrically conducting particles.

4. The method according to claim 3, wherein the electrically conducting particles are selected from the group consisting of gold, silver, glassy carbon, graphite, and carbon nanotubes.

5. The method according to claim 3, wherein the polymeric matrix comprises a gradient of the electrically conducting particles which increases in concentration away from a sample contact surface.

6. The method according to claim 1, wherein the polymeric matrix comprises a gradient of the ionophore potassium tetrakis (4-chlorophenyl)borate molecule which increases in concentration towards a sample contact surface.

7. The method according to claim 1, wherein:
the conductivity increasing salts are lipophilic, and
the conductivity increasing salts are selected from the group consisting of tetradodecylammonium tetrakis(4-chlorophenyl)borate (ETH 500) and borates ($BR_4^-$).

8. A wide range ion-selective polymeric matrix comprising 32% by weight of a Poly(vinylchloride) polymer, 65% by weight of a Mesamoll plasticizer, 2% by weight of an ionophoric potassium tetrakis (4-chlorophenyl)borate molecule and comprising one or more conductivity increasing salts, wherein said ion-selective polymeric matrix is sensitive to organic ions and ionisable organic molecules with logP values above 0, wherein said ion-selective polymeric matrix is not preloaded with said organic ions or said ionisable organic molecules with logP values above 0.

9. The wide range ion-selective polymeric matrix according to claim 8, wherein said conductivity increasing salts are present in an amount up to 20% by weight.

10. The wide range ion-selective polymeric matrix according to claim 8, wherein the polymeric matrix further comprises electrically conducting particles.

11. The wide range ion-selective polymeric matrix according to claim 10, wherein the electrically conducting particles are selected from the group consisting of gold, silver, glassy carbon, graphite, and carbon nanotubes.

12. A potentiometric electrode comprising the wide range ion-selective polymeric matrix according to claim 8.

13. The wide range ion-selective polymeric matrix according to claim 10, wherein the polymeric matrix comprises a gradient of the electrically conducting particles which increases in concentration away from a sample contact surface.

14. The wide range ion-selective polymeric matrix according to claim 8, wherein the polymeric matrix comprises a gradient of the ionophoric potassium tetrakis (4-chlorophenyl)borate molecule which increases in concentration towards a sample contact surface.

15. The wide range ion-selective polymeric matrix according to claim 8, wherein:
the conductivity increasing salts are lipophilic, and
the conductivity increasing salts are selected from the group consisting of tetradodecylammonium tetrakis(4-chlorophenyl)borate (ETH 500) and borates ($BR_4^-$).

* * * * *

UNITED STATES PATENT AND TRADEMARK OFFICE
CERTIFICATE OF CORRECTION

PATENT NO. : 10,018,584 B2
APPLICATION NO. : 14/405923
DATED : July 10, 2018
INVENTOR(S) : Hugo Bohets Page 1 of 1

It is certified that error appears in the above-identified patent and that said Letters Patent is hereby corrected as shown below:

On the Title Page

Column 2, item (57), Abstract, Line 8:
"of organic ions an ionizable organic molecules. As opposed"
Should read:
--of organic ions and ionizable organic molecules. As opposed--; and In the Specification Column 5, Line 35:
"as will become evident form the examples hereinafter,"
Should read:
--as will become evident from the examples hereinafter,--; and Column 9, Line 34:
"($ZnO_{2+}$, $Zn^{2+}$). In the present state of the art there is one ISE"
Should read:
--($ZnO^{2+}$, $Zn^{2+}$). In the present state of the art there is one ISE--; and Column 9, Line 37:
"titrations using one ISE proofs the truly universal character"
Should read:
--titrations using one ISE proves the truly universal character--.

Signed and Sealed this
Twenty-third Day of April, 2019

Andrei Iancu
*Director of the United States Patent and Trademark Office*